US005972350A

United States Patent [19]
Atherton et al.

[11] Patent Number: 5,972,350
[45] Date of Patent: Oct. 26, 1999

[54] **FELINE VACCINES CONTAINING *CHLAMYDIA PSITTACI* AND METHOD FOR MAKING THE SAME**

[75] Inventors: Rebecca A. Atherton, Shawnee, Kans.; Norbert Schmeer, Haan, Germany; Jean A. Hallstrom, Merriam; Jennifer K. Lane, Shawnee, both of Kans.; Kristina J. Hennessy, Parkville, Mo.

[73] Assignees: Bayer Corporation, Pittsburgh, Pa.; Baker Aktiengesellschaft, Leverkusen, Germany

[21] Appl. No.: 08/643,673

[22] Filed: May 6, 1996

[51] Int. Cl.[6] ...................... A61K 39/118; G01N 33/554; G01N 33/53; C07K 16/00

[52] U.S. Cl. .................... 424/263.1; 435/7.32; 435/7.36; 435/7.94; 530/388.2; 530/389.5

[58] Field of Search ................................ 435/7.32, 7.36, 435/7.44; 530/388.2, 389.5; 424/263.1

[56] References Cited

U.S. PATENT DOCUMENTS 5,242,686 9/1993 Chu et al. ................................ 424/92

FOREIGN PATENT DOCUMENTS

95/12411 5/1995 WIPO .

OTHER PUBLICATIONS

VesiKari, T., "Clinical & Immunological Studies of Rotavirus Vaccines." Southeast Asain. J. Trop. Med. PV6L. HLHH. 19(3):437–447, 1988.

Wasmoen et al, "Demonstration of One Year Duration of Immunitu for an Inactivated Feline *Chlamydia psittaci* Vaccine" Fel. Pract. 20(3):13–16, 1992.

Clemens et al "Impact of H. influezal Type B Polysaccharide–Tetamus Protein Conjagale Vaccine on Respones to Concurrently Administered D–T–P Vaccine" JAMA 267(5):673–678, 1992.

Umino et al "Improvement in Potency Assay of MMR Trivalent Vaccines" J. Virol. Meth. 27:159–168, 1990.

Vaccine, vol. 13, No. 8, Gareth E. Jones et al, (month unavailable) 1995, pp. 715–723. No Title.

Infection and Immunity, vol. 64, No. 4, Apr. 1996, D. Vanrompay et al, pp. 1265–1271. No Title.

Biological Abstracts, vol. 94, No. 3, 1992, Abstract No. 29505, D. Vanrompay et al. No Title.

Robert M. Cello, D.V.M., Am. J. Vet. Med. Assoc. 158:932–938, (Month unavailable) 1971.

Shewen et al ( Can. J. Comp. Vet. Res. 44:244–251, Jul. 1980).

McKercher (Am. J. Vet. Res. 13:557–561, Oct. 1952).

*Primary Examiner*—James C. Housel
*Assistant Examiner*—Rodney P. Swartz
*Attorney, Agent, or Firm*—Joseph C. Gil; Godfried R. Akorli

[57] ABSTRACT

The present invention relates to feline vaccines comprising inactivated a non reactive *Chlamydia psittaci* for prevention and treatment of chlamydia diseases in cats.

1 Claim, 1 Drawing Sheet

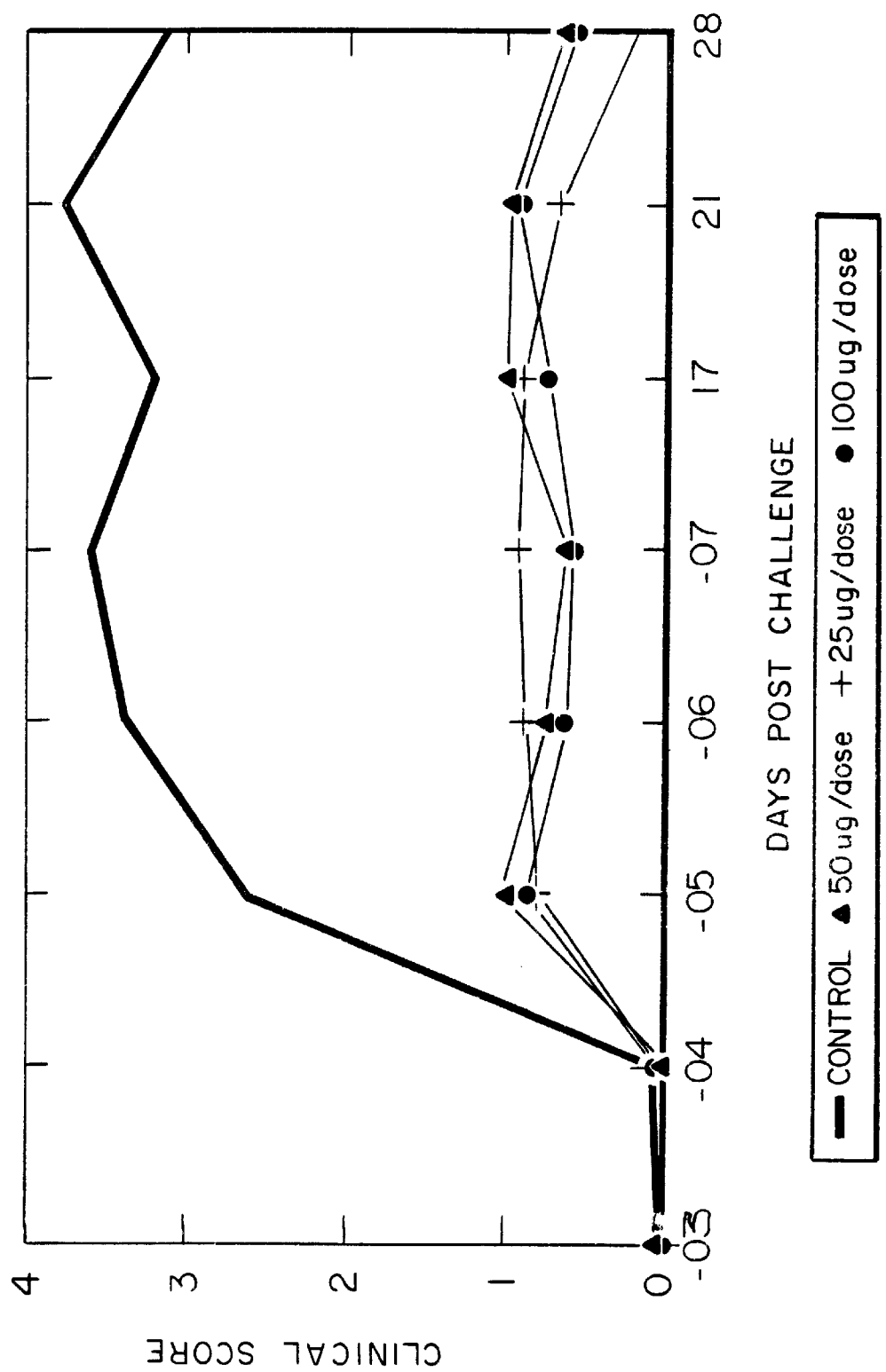

FELINE VACCINES CONTAINING *CHLAMYDIA PSITTACI* AND METHOD FOR MAKING THE SAME

BACKGROUND OF THE INVENTION

Feline chlamydiosis is a common conjunctival and respiratory disease of cats known as feline pneumonitis (FPn). This highly contagious disease is characterized by sneezing and coughing and is accompanied by mucopurulent ocular and nasal discharges. All age groups of cats are susceptible and, although mortality is not great, infected kittens and older cats may become severely debilitated. Because of its extreme infectivity, feline chlamydiosis constitutes a major problem in pet hospitals, clinics and catteries. There is some thought that persistent genital tract infection by *Chlamydia psittaci* is a cause of reproductive failure in catteries.

Vaccination studies with modified-live compositions of *Chlamydia psittaci* have produced conflicting results. Cello (Am. J. Vet. Med. Assoc. 158:932–938, 1971) indicated that such vaccines demonstrated no significant protection of cats. Shewen, et al. (Can. J. Comp. Vet. Res. 44:244–251, 1980) indicated partial protection while McKercher (Am. J. Vet. Res. 13:557–561, 1952) and others indicated almost complete protection by such vaccines. However, because the vaccinated cats are receiving live *Chlamydia psittaci.* some vaccine organisms can shed to other cats and reversion has been proposed to occur.

Studies with inactivated chlamydia vaccines have produced mixed results and unacceptable local and systemic reactions in vaccinated cats. Comparative challenge studies conducted with four inactivated vaccine preparations and a commercial modified-live vaccine demonstrated that the inactivated preparations conferred virtually no protection against chlamydia infection in cats (Shewen et al, Can. J. Comp. Med. 44:244–30 251, 1980). An inactivated Chlamydia psittaci vaccine has been described by Chu et al. (U.S. Pat. No. 5,242,686). However, this vaccine is not purified and causes unacceptable local reactions when administered to cats (COMPENDIUM).

With the knowledge that modified-live chlamydia vaccines can shed to other animals, can recombine with field strains of *Chlamydia psittaci* and can revert to virulence, and the knowledge that currently-marketed inactivated chlamydia vaccines are either ineffective or cause unacceptable local reactions, there is a need for effective, non-reactive chlamydia vaccines. It is an object of the present invention to provide an inactivated feline chlamydia vaccine composition having high immunogenicity without having a high antigenic mass. It is another object of this invention to provide a simple process for producing a suitable purified *Chlamydia psittaci* for production of a non-reactive, effective vaccine as a monovalent preparation or in a combination with other feline antigens.

The present invention discloses an inactivated, immunogenically effective *Chlamydia psittaci* which is incorporated into chlamydia vaccines in minute quantities (low antigen load or low antigen mass) and which is purified away from the cells in which it is grown so as to produce a vaccine which, when administered to cats is non-reactive but highly effective. In such vaccine the immunogenically effective, low antigen mass, purified *Chlamydia psittaci* is combined with effective amounts of an adjuvant and a pharmaceutically acceptable carrier or diluent therefor. The purification process for production of the *Chlamydia psittaci* incorporates several steps which include use of the yolk sac membrane, washed free of yolk material, as seed to inoculate a mammalian cell line such as the Buffalo Green Monkey (BGM) cell line available from Bio Whittaker and, after completion of the cell destruction by the chlamydia (cytopathic effect or CPE), removing the cells and cellular debris from the vaccine preparation prior to inactivation. One of the major requirements of this invention is that the cell line used for growth of the *Chlamydia psittaci* be destroyed by the organism within 7 days of infection with the *Chlamydia psittaci* (demonstrate at least 80% CPE within 7 days of infection with the chlamydia).

BRIEF DESCRIPTION OF THE DRAWINGS

FIG. 1 is a graph of a group summary of clinical scores (mean score/day which is further reported in Table 1: showing that minute quantities of *Chlamydia psittacci* (less than 50 µg/dose), when made into a vaccine, protected as well as large amounts of *Chlamydia psittaci* (50–1000 µg/mL as noted by Chu et al.).

DETAILED DESCRIPTION OF THE INVENTION

The present invention provides a vaccine composition comprising a minute quantity of a purified, inactivated, immunogenically effective amount of *Chlamydia psittaci* in combination with an effective amount of an adjuvant; and a pharmaceutically acceptable carrier or diluent therefor which may be combined with other feline antigens. When administered to cats, the vaccine is non-reactive but highly effective.

As used herein, the term "immunogenically effective amount" refers to the ability of the *Chlamydia psittaci* in the vaccine to protect cats from infection with *Chlamydia psittaci* after they have been vaccinated. The term "minute quantity" refers to the amount of *Chlamydia psittaci* added to the vaccine being less than 50 µg/dose. The term "purified" refers to processes which eliminate the presence of egg yolk material in the final vaccine. These processes include but are not limited to inoculating the tissue culture with egg yolk sac membrane which has been washed free of egg yolk material with saline, ground and resuspended in phosphate buffered saline, using a cell line which is destroyed by the *Chlamydia psittaci* and removing the cells and cellular debris prior to inactivating the *Chlamydia psittaci*.

The present invention also includes a process for preparing a vaccine composition against chlamydia infections comprising culturing *Chlamydia psittaci* in egg yolk sac, harvesting egg yolk sac membrane from said egg yolk sac and freezing it as a master seed, culturing said master seed or passages of said master seed in a highly susceptible cell line growing on a surface until at least 80% of the cell line is destroyed by the *Chlamydia psittaci,* harvesting the destroyed susceptible cell line and media containing the *Chlamydia psittaci* accompanying said cell line, removing the destroyed cell line from the *Chlamydia psittaci,* inactivating the *Chlamydia psittaci* and mixing the inactivated *Chlamydia psittaci* with an adjuvant and physiologically acceptable carrier.

*Chlamydia psittaci* has a development cycle with distinct reproductive (reticulate bodies) and infectious (elementary bodies) forms. When grown in the cell lines most commonly used for growth of Chlamydia (e.g. Dog Kidney cells, McCoy cells and CRFK cells) this organism does not produce a complete cytopathic effect on the cell sheet. This makes optimal time of harvest difficult to determine in a production setting. It also produces Chlamydia organisms with low immunogenicity such that they need to be multiply harvested from the cells or highly concentrated after harvest. In some cases (described in U.S. Pat. No. 5,242,686) they must be inactivated in the subculture. These procedures result in a vaccine which has high antigen load (high antigen mass containing 50 to 1000 μg/dose) and which is reactive to cats post vaccination. Infection of cells, such as the Buffalo Green Monkey kidney cell line, which are highly susceptible to infection with *Chlamydia psittaci* organisms, results in complete destruction of the cell sheet at which time the number of infectious organisms in the culture is very high. These organisms can be easily purified away from the cells and cellular debris by filtration, centrifugation or ultrafiltration and a minute quantity of the harvested purified *Chlamydia psittaci* (<50 μg/dose) is immunogenically effective when formulated into a vaccine containing an adjuvant and an acceptable pharmaceutical carrier.

According to the invention, a chlamydia isolate such as the Cello strain of *Chlamydia psittaci* was first propagated in the yolk sac membrane of embryonated chicken eggs. The *Chlamydia psittaci* isolate was inoculated into the yolk sac of embryonated chicken eggs and incubated at 37° C. for 5–10 days. The eggs were candled daily starting at day 5 to determine viability. On the day that 25% of the eggs had died, the yolk sac membranes of the still-viable eggs were harvested, washed with phosphate buffered saline to remove excess egg yolk protein material and aseptically blended, resuspending the blended membrane in phosphate buffered saline. One milliliter aliquots of this blended and resuspended seed material were stored frozen at −70° C. Up to 5 passages of this seed is made using the same procedure to prepare the production seed useful for inoculating tissue culture cells.

Production of the *Chlamydia psittaci* vaccine antigen is accomplished by first preparing the tissue cell culture. Buffalo Green Monkey kidney cells were grown in Dulbecco's MEM with high glucose (DMEM/H), 5% fetal bovine serum, 10 mM HEPES buffer and neomycin. When the cells were confluent they were infected with *Chlamydia psittaci* in DMEM/H with neomycin. The *Chlamydia psittaci* was adsorbed onto the cells with a low volume of media and then more DMEM/H media was added. The infected cells were incubated at 37° C. for 5 to 7 days. Normally, by day 6 post-infection 90–100% of the cell sheet was destroyed. At this point the *Chlamydia psittaci* was harvested (harvest fluids) by swirling the vessels to remove any remaining cells. The cells and cell debris were removed from the harvest fluids by 5μ filtration or by centrifugation. Then the purified harvest fluids were inactivated. Inactivating agents include but are not limited to binary ethylenimine, formalin, thimerosal and betapropiolactone. The pH was adjusted to neutral and the purified harvest fluids were adjusted to an immunogenically effective amount for formulation with adjuvant by dilution in phosphate buffered saline. The immunogenically effective amount of *Chlamydia psittaci* was usually less than 50 μg/dose and preferably less than 10 μg/dose. Any adjuvant may be used. Non-limiting examples of adjuvants used in the present invention are polymers and co-polymers, acrylic acid polymers and co-polymers, polyacrylic acid such as Carbopol®, surfactants such as hexadecylamine, saponin, Quil A, aluminum hydroxide, aluminum phosphate, peptides such as muramyl dipeptide, oil emulsions, immunomodulators such as interleukins and interferons, interferon inducers, ethylene maleic anhydride copolymers such as EMA-31, NEOCRYL A640 and POLYGEN® (supplied by MVP Laboratories). Mixtures of any of the above adjuvants or adjuvant systems can also be used.

It has been discovered that adjuvants described above will act in effective amounts between 0.01% and 50% v/v of the total vaccine dose. Preferably, the concentration of adjuvant will be adjusted between 1% and 15%. More preferably, POLYGEN® is used at concentrations between 1% and 5% and Carbopol® is used at concentrations between 0.1% and 0.5%.

The vaccine composition of the present invention also comprises a pharmaceutically acceptable carrier or diluent and may include additional feline antigens such as antigens for feline rhinotracheitis, feline leukemia, feline calicivirus and feline panleukopenia, feline immunodeficiency virus, feline infectious peritonitis, *Toxoplasma gondii* and rabies.

TABLE 1

GROUP SUMMARY OF CLINICAL SCORES - MEAN SCORE/DAY

| Day | Control Group | 25 μL Antigen Mass | 50 μL Antigen Mass | 100 μL Antigen Mass |
|---|---|---|---|---|
| −3 | 0.00 | 0.00 | 0.00 | 0.00 |
| 1 | 0.05 | 0.00 | 0.00 | 0.05 |
| 5 | 2.63 | 0.78 | 1.00 | 0.85 |
| 9 | 3.38 | 0.88 | 0.75 | 0.63 |
| 13 | 3.60 | 0.93 | 0.63 | 0.58 |
| 17 | 3.23 | 0.90 | 1.00 | 0.73 |
| 21 | 3.76 | 0.68 | 0.98 | 0.93 |
| 25 | 3.15 | 0.20 | 0.65 | 0.60 |
| Average of Days 5–28 | 3.29 | 0.73 | 0.83 | 0.72 |

Table 2 demonstrates that a multicomponent vaccine containing inactivated Feline Rhinotracheitis, Feline Calicivirus, Feline Panleukopenia virus, Feline Leukemia virus and Feline *Chlamydia psittaci* prepared according to this invention is efficacious.

TABLE 2

RESULTS OF EFFICACY TESTING OF 5-WAY FELINE VACCINE CONTAINING FELINE CHLAMYDIA PSITTACI, FELINE RHINOTRACHEITIS FELINE LEUKEMIA, FELINE CALICIVIRUS AND FELINE PANLEUKOPENIA VIRUS

| CHALLENGE ANTIGEN | TITER RESPONSE NO. >1:8/TOTAL | PROTECTION |
|---|---|---|
| FELINE PANLEUKOPENIA | | |
| SC | 4/4 | 100% |
| IM | 4/4 | 100% |
| CONT | 0/4 | 0% |
| FELINE LEUKEMIA | | |
| SC | NA | 80% |
| IM | NA | 90% |
| CONT | NA | 22% |
| FELINE SC | NA | EXCELLENT "T" = 34 VACC C.M. = 9.7 CONT. C.M. = 49.3 |
| RHINOTRACHEITIS IM | NA | EXCELLENT "T" = 34 VACC C.M. = 8.3 CONT. C.M. = 49.3 |
| CONT | NA | NONE |
| FELINE CALICIVIRUS | | |
| SC | NA | EXCELLENT "T" = 34 VACC C.M. = 9.0 CONT C.M. = 20.0 |
| IM | NA | EXCELLENT "T" = 34 VACC C.M. = 4.7 CONT C.M. = 20.0 |
| CONT | NA | NONE |

TABLE 2-continued

RESULTS OF EFFICACY TESTING OF 5-WAY FELINE VACCINE CONTAINING FELINE CHLAMYDIA PSITTACI, FELINE RHINOTRACHEITIS FELINE LEUKEMIA, FELINE CALICIVIRUS AND FELINE PANLEUKOPENIA VIRUS

| CHALLENGE ANTIGEN | TITER RESPONSE NO. >1:8/TOTAL | PROTECTION |
|---|---|---|
| FELINE CHLAMYDIA PSITTACI | | |
| SC | NA | EXCELLENT AV. MS = 0.54 |
| IM | NA | EXCELLENT AV. M.S. = 0.49 |
| CONT | NA | NONE AV. M.S. = 2.04 |

C.M. = CUMULATIVE MEAN SCORE
AV. M.S. = AVERAGE MEAN SCORE
"T" = A STATISTICAL CALCULATION (one-tailed, Mann whitney modification of Wilcoxon's two samples test) COMPARING THE CLINICAL SCORES OF VACCINATES WITH THOSE OF CONTROLS (DEFINED BY 9 CFR 115.130, 113.149, 113.131, 115.150, SAM 310 AND SAM 311. A "T" OF ≧31 IS EQUIVALENT TO PROTECTION.

As further embodiments of the present invention, the vaccine composition can be administered as sustained release product(s), e.g. formulated with lactide-glycolide copolymer, microparticles which produce sustained release and as an implant.

The present invention also provides a method for preventing chlamydia infection in felines comprising administering to a feline an immunogenically effective amount of the vaccine composition described above. The routes of administration of the present invention are parenteral (subcutaneous, intramuscular, intraperitoneal and intradermal) or oral/nasal. The preferred routes of administration are subcutaneous and intramuscular. It has been discovered that an effective regimen of treatment includes administering the vaccine composition at least about two times with each administration separated by about two to about four weeks, preferably from about fourteen to about thirty days.

The working examples set forth below are intended to illustrate the invention without limiting its scope.

EXAMPLES

Example 1

Monovalent Feline *Chlamydia psittaci*

Cell stock of Buffalo Green Monkey kidney cells were thawed, added to growth medium containing DMEM/H+5% fetal bovine serum, 10 mM HEPES buffer and 30 μg/mL of Neomycin and centrifuged for 10 to 15 minutes at 400–600× g. Centrifuged cell stock was suspended in fresh growth medium and planted into roller bottles. The roller bottles were incubated rotating at 37° C. until the cells grew to confluency. Subcultures of the cells were made until the desired number of roller bottles for production purposes were obtained. Usually production lots vary from 50 to 500 roller bottles. When the production subculture roller bottles of the BGM cells were 3–5 days old and at least 95% confluent, the growth medium was removed and *Chlamydia psittaci* seed was added at a multiplicity of infection (MOI) of 0.01 to 0.1. The medium used for Chlamydia growth was DMEM/H plus 30 μg/mL Neomycin. The roller bottles were reincubated for adsorption of the Chlamydia at 36–38° C. for one hour and then 200 mL more of media was added to each roller bottle. Incubation at 36–38° C. was continued for 5–7 days or until CPE was >80%. Roller bottle fluids were harvested by shaking the roller bottles to remove any remaining cells from the surface and transferring the harvest fluids into a container. Harvested fluids were clarified (purified) by filtration through a 5 micron polypropylene filter to remove extraneous cell debris. The clarified fluids were inactivated with 0.01 M Binary Ethylenimine (BEI) for 72 hours at 2–8° C. After inactivation, the BEI was neutralized with Sodium Thiosulfate at a 0.02 M final concentration.

The purified, inactivated *Chlamydia psittaci* was diluted to three different levels of antigen (three different antigenic masses). The highest antigenic mass tested was 100 μL/dose which was equivalent to approximately 100 μg/dose, the intermediate antigen mass tested was 50 μL/dose which was approximately equivalent to 50 μg/dose while the lowest antigen mass tested was 25 μL/dose or approximately 25 μg/dose. All antigenic masses were diluted with phosphate buffered saline so as to q.s. each preparation to 0.95 mL. A volume of 0.05 mL of POLYGEN® was added to each preparation as an adjuvant in order to prepare the final vaccines. One milliliter doses of these vaccines were administered to groups of 5 seronegative cats at a 3 week interval. The first dose was administered on day 0 and the second dose was administered at day 21. A group of 5 seronegative cats, matched in age and environment, were not vaccinated but held as nonvaccinated controls. All cats were challenged both intra-nasally and intra-ocularly with virulent *Chlamydia psittaci* at 2–8 weeks post booster with the second dose. All cats were monitored daily for 28 days for clinical signs of *Chlamydia psittaci* disease including body temperature, ocular discharge, conjunctivitis, nasal exudate, sneezing, coughing, dyspnea, anorexia, dehydration and depression. A weighted scoring system was used to analyze the data. The more serious signs of disease were given higher numerical values. All data were statistically analyzed in 4-day intervals and are presented in Table 1. These data are graphically presented in FIG. 1.

The results presented in Table 1 and FIG. 1 clearly demonstrate that the *Chlamydia psittaci* when prepared according to this invention is efficacious at antigenic masses of as little as 25 μg/dose. Since this low antigenic mass vaccine conferred protection equivalent to the high antigenic mass vaccine, it is expected that levels below 25 μg/dose, when prepared according to the method of the present invention, would also be protective.

Example 2

Inactivated feline *Chlamydia psittaci* prepared according to EXAMPLE 1 of this invention was mixed with four other inactivated feline antigens to prepare a multicomponent vaccine. Thirty-five microliters of POLYGEN® adjuvanted *Chlamydia psittaci* ($10^{6.0}$ $TCID_{50}$/mL) were mixed with feline leukemia at an antigenic dose of 1.25 ELISA relative potency units/dose adjuvanted with POLYGEN®, $10^{8.0}$ $TCID_{50}$/dose of POLYGEN® adjuvanted Feline Rhinotracheitis, $10^{7.8}$ $TCID_{50}$/dose of POLYGEN® adjuvanted Feline Calicivirus and $10^{5.9}$ $TCID_{50}$/dose of POLYGEN® adjuvanted Feline Panleukopenia virus. This 5-way vaccine was tested for efficacy in vaccination/challenge tests conducted in cats. At the outset of the experiment, all cats were bled for serum and whole blood samples. Sera were screened for antibody to Feline Rhinotracheitis, Feline Calicivirus and Feline Panleukopenia virus titers. All cats started with titers less than 1:2 for those viruses. The cats used in the FeLV protocol were negative for p27 antigen. Five groups of cats (n=74), 13–15 weeks of age, were vaccinated and boostered three weeks later with 1.0 mL of the 5-way vaccine. Approximately ½ of the cats were vaccinated subcutaneously and ½ were vaccinated intramuscularly.

Eight vaccinated (4 subcutaneous and 4 intramuscular) cats and one control cat were evaluated for serological response to Feline Panleukopenia post vaccination and booster. A serological response of 1:8 is considered to be protective for this component. The post vaccination results are listed in Table 2.

Twelve 5-way vaccinated (6 subcutaneously and 6 intramuscularly) cats and 4 nonvaccinated control cats were challenged with virulent Feline Rhinotracheitis virus. Throat swabs and blood samples were taken pre challenge. All cats were monitored for signs of disease post challenge. Clinical disease signs and temperatures were recorded and analyzed with mean scores presented in Table 2. Efficacy is demonstrated by a statistically significant difference in clinical scores between vaccinates and controls.

Twelve 5-way vaccinated (6 subcutaneously and 6 intramuscularly) cats and 4 nonvaccinated control cats were challenged with virulent Feline Calicivirus. Throat swabs and blood samples were taken post challenge. Additionally, cats were monitored for temperature and clinical signs of disease. Clinical signs were recorded, scored and analyzed and are presented in Table 2. Efficacy is demonstrated by a statistically significant difference in clinical scores between vaccinates and controls.

Twenty 5-way vaccinated (10 subcutaneously and 10 intramuscularly) cats and 10 nonvaccinated control cats were challenged with virulent Feline *Chlamydia psittaci* and monitored and scored for clinical signs of disease as described in EXAMPLE 1. Efficacy is demonstrated by a statistically significant difference between vaccinate and control mean scores. Summary results of this challenge are also shown in Table 2.

Twenty-two 5-way vaccinated (11 subcutaneously and 11 intramuscularly) cats and 9 nonvaccinated control cats were challenged with virulent FeLV. This challenge requires that the cats first be immunosuppressed and challenged for 2 consecutive days. Cats were checked from week 3 to week 12 post challenge for viremia by detection of p27 antigen in the blood using an indirect immunofluorescence assay (IFA). Protection was determined using the guidelines as described in Shibley et al. (JAVMA 1991, 199: 1402–1406.) and are presented in Table 2.

It is evident from Table 2 that all 5 components of this multicomponent vaccine comprising the feline *Chlamydia psittaci* of this invention were efficacious. It should also be noted that none of the vaccinates in this study nor any vaccinates in other studies conducted on the *Chlamydia psittaci* vaccine or a multicomponent vaccine comprising the *Chlamydia psittaci* demonstrated local or systemic reactions to the vaccine. The low antigen mass *Chlamydia psittaci* was the major reason for this lack of reactivity.

While the invention has been described with respect to the above specific embodiments, it should be recognized that various modifications and changes which may be apparent to those skilled in the art to which the invention pertains may be made and also fall within the scope of the invention as defined by the claims that follow:

What is claimed is:

1. An inactivated, immunogenically effective *Chlamydia psittaci* vaccine which does not produce local and systemic adverse reactions, containing a minute quantity of purified *Chlamydia psittaci*.

* * * * *